US008613234B1

(12) United States Patent
Harrell

(10) Patent No.: US 8,613,234 B1
(45) Date of Patent: Dec. 24, 2013

(54) SOIL SAMPLING APPARATUS

(76) Inventor: Linford L. Harrell, West Point, VA (US)

( * ) Notice: Subject to any disclaimer, the term of this patent is extended or adjusted under 35 U.S.C. 154(b) by 137 days.

(21) Appl. No.: 13/374,491

(22) Filed: Jan. 3, 2012

Related U.S. Application Data

(60) Provisional application No. 61/516,869, filed on Apr. 11, 2011.

(51) Int. Cl.
*G01N 1/28* (2006.01)
*A01B 45/02* (2006.01)

(52) U.S. Cl.
USPC .......................................... 73/864.41; 172/22

(58) Field of Classification Search
USPC .................. 73/864.44, 865.45; 172/22
See application file for complete search history.

(56) References Cited

U.S. PATENT DOCUMENTS

| | | | | |
|---|---|---|---|---|
| 2,543,888 A | * | 3/1951 | Bunch | 111/91 |
| 2,643,858 A | | 6/1953 | Hardman | |
| 3,022,833 A | * | 2/1962 | Reaser | 172/19 |
| 3,125,883 A | * | 3/1964 | Wollner | 73/864.44 |
| 3,171,498 A | * | 3/1965 | Logan | 172/22 |
| 3,224,512 A | | 12/1965 | Alexander | |
| 3,264,877 A | | 8/1966 | Boxrud | |
| 3,331,249 A | * | 7/1967 | Boxrud | 73/864.31 |
| 3,464,504 A | * | 9/1969 | Stange | 173/28 |
| 3,625,296 A | | 12/1971 | Mabry | |
| 4,316,393 A | | 2/1982 | Philipenko | |
| RE30,901 E | * | 4/1982 | Boxrud | 73/864.31 |
| 4,326,591 A | * | 4/1982 | Dedoes | 172/22 |
| 4,828,047 A | * | 5/1989 | Rogerson | 173/24 |
| 4,869,115 A | * | 9/1989 | Edwards et al. | 73/864.31 |
| 5,076,372 A | | 12/1991 | Hellbusch | |
| 5,211,248 A | | 5/1993 | Nosewicz et al. | |
| 5,419,211 A | | 5/1995 | Rodel et al. | |
| 5,435,399 A | | 7/1995 | Peterson et al. | |
| 5,592,805 A | * | 1/1997 | Croft | 56/16.4 R |
| 5,741,983 A | | 4/1998 | Skotnikov et al. | |
| 5,816,336 A | * | 10/1998 | Underhill | 172/22 |
| 5,887,491 A | | 3/1999 | Monson et al. | |
| 6,016,713 A | * | 1/2000 | Hale | 73/864.45 |
| 6,138,590 A | | 10/2000 | Colburn, Jr. | |
| 6,192,991 B1 | * | 2/2001 | Seliga et al. | 172/22 |
| 6,260,633 B1 | | 7/2001 | Machek et al. | |
| 6,363,803 B1 | | 4/2002 | Hubers | |

(Continued)

FOREIGN PATENT DOCUMENTS

| | | |
|---|---|---|
| DE | 3612409 | 10/1987 |
| DE | 3612410 | 10/1987 |

*Primary Examiner* — Hezron E Williams
*Assistant Examiner* — Mark A Shabman
(74) *Attorney, Agent, or Firm* — William G. Sykes

(57) ABSTRACT

A soil sampler having a hollow, ground-contacting drum having a hollow, tapered probe projecting outwardly therefrom for extracting soil plugs. Each soil plug is discharged by gravity into the drum interior. As the drum rotates, all soil plugs are blended with each other. After soil plug collection, the drum is raised and a chute is inserted into the drum. As the drum continues to rotate, the blended soil sample falls from the top of the drum into the chute, slides down the chute and is deposited into a removable cup on a horizontal circular platform of a soil collection carousel assembly. The circular platform is then rotated to bring a new, empty cup into position to receive the next blended sample. The soil sampler is mounted on a trailer drawn by a truck or tractor. All functions are remotely controlled from the cab of the truck or tractor.

15 Claims, 9 Drawing Sheets

(56) References Cited

U.S. PATENT DOCUMENTS

| | | |
|---|---|---|
| 6,487,920 B1 | 12/2002 | Robbat, Jr. |
| 6,488,100 B2 * | 12/2002 | Underhill ........................ 172/22 |
| 6,766,865 B1 * | 7/2004 | Dagel et al. ..................... 172/22 |
| 7,216,555 B2 | 5/2007 | Drummond et al. |
| 7,677,119 B2 | 3/2010 | Garel |
| 7,827,873 B2 | 11/2010 | Burton |
| 7,836,972 B2 | 11/2010 | Pavlik |
| 2011/0162855 A1 * | 7/2011 | Vincel .............................. 172/1 |

* cited by examiner

SOIL SAMPLING APPARATUS

RELATED APPLICATIONS

This application claims priority in accordance with 37 U.S.C. §1.119(e) to U.S. Provisional Patent Application No. 61/516,869 filed Apr. 11, 2011 and which is included herein in its entirety by reference.

FIELD OF THE INVENTION

The invention pertains to soil sampling apparatus and, more particularly, to a semi-automatic, vehicle drawn soil sampling apparatus.

BACKGROUND OF THE INVENTION

Agronomy is the branch of agriculture dealing with field-crop production and soil management. Modern field crop farming relies on precision treatment of the soil. However, no soil treatment is possible before soil analysis indicates the precise treatment required.

The types of soil and climate in a given area, determine to a great extent, the kind of farming and the various crops that can be successfully grown at such location. Within any given area there are many kinds of soil having certain properties that require different land practices based on the residual and natural level of fertility. Because of these inherent variations, soil analysis has become a highly specialized field of endeavor for the chemical and fertilizer industry. Through research and experimentation these specialists have come to know what to expect of different types of soil and how to best supplement each particular type to produce maximum crop yield.

A good laboratory soil test and recommendation is primarily predicated on a reliable soil sample. Said test and any recommendations derived therefrom are only as reliable and accurate as the composite sample taken from the soil strata. Conversely, a poor soil sample can result in recommendations which are misleading to the producer and can cause lower yields due to the improper use of supplements. Before discovery of the subject invention, the conventional method of taking soil samples has been by the use of a clean bucket and a spade or by the use of a simple soil auger. Such methods are laborious, expensive, and time consuming and to say the least, not always reliable as the sampling operation is in such instances always subject to the element of error on the part of the sampler.

DISCUSSION OF THE RELATED ART

Attempts may be found in the prior art to provide some aspects of the present invention. For example, U.S. Reissue Pat. No. RE 30,901 for SOIL SAMPLING DEVICE, reissued Apr. 13, 1982 to Phillip P. Boxrud teaches a device for attachment to the drawbar of a tractor or similar vehicle for removing cores of soil from the ground. A plurality of hollow probes is mounted on the perimeter of a drum that may be lowered by a hydraulic cylinder to make contact with the ground. As the drum rotates, core samples are removed from the ground and deposited into the interior of the drum.

The RE 30,901 patent to BOXRUD is not seen to teach or suggest the novel soil sampling apparatus of the present invention.

SUMMARY OF THE INVENTION

In accordance with the present invention there is provided a soil sampling apparatus consisting of a hollow, ground-contacting drum having a hollow, tapered probe projecting outwardly from a central perimeter of the drum. The probe is communicative with an interior region of the drum and serves to extract soil plugs from the ground as the drum rolls therealong. Each soil plug is discharged by gravity from the probe and falls into the interior of the drum. As the drum rotates, all soil plugs are mixed with each other within the drum.

Once soil plugs from the desired area are collected, the drum is raised and rotated with a motor to continue to blend the combined soil sample. A chute is then inserted into an opening in the side of the drum. As the drum continues to rotate, the blended soil sample falls from the top of the drum into the chute. The blended sample slides down the chute and is deposited into a removable sample collection cup retained in a sample cup receptacle disposed on the upper surface of a horizontal circular platform forming a part of a soil collection carousel assembly. Once the sample is in the collection cup, the horizontal circular platform is rotated to bring a new, empty sample collection cup into position to receive the next blended sample.

The soil sample assembly is mounted on a trailer and may be pulled behind a truck or tractor. All functions are remotely controlled from the cab of the truck or. tractor It is, therefore, an object of the invention to provide a mobile, automatic soil sampling apparatus for removing multiple soil samples from a traversed area.

It is another object of the invention to provide a mobile, automatic soil sampling apparatus comprising a drum and at least one tapered soil sampling probe connected thereto.

It is an additional object of the invention to provide a mobile, automatic soil sampling apparatus wherein a sample collecting drum is movable between a lowered, sampling position and a raised position.

It is a further object of the invention to provide a mobile, automatic soil sampling apparatus wherein multiple samples from a desired sampling area are blended and then collected in a container.

It is a still further object of the invention to provide a mobile, automatic soil sampling apparatus wherein multiple, selectable soil sample containers are provided and multiple areas, each producing a unique blended sample, may be sampled without human intervention.

It is yet another object of the invention to provide a mobile, automatic soil sampling apparatus wherein all operations involved are controlled by a remote control panel.

It is another object of the invention to provide a mobile, automatic soil sampling apparatus wherein a television camera is disposed to remotely monitor operation of the soil collection apparatus.

It is an additional object of the invention to provide a mobile, automatic soil sampling apparatus wherein during a blended sample discharge, soil sampling probes are cleaned.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

The present invention provides a soil sampling apparatus for pulling behind a tow vehicle such as a tractor, truck, etc. The novel soil sampling apparatus periodically extracts a plug of soil using an interchangeable, tapered soil probe. The extracted soil sample is discharged into the interior region of a rotating drum where it is mixed with other soil samples. When a desired length of a field has been sampled, the mixed soil samples are discharged into a numbered collection cup disposed on a rotary sample collection carousel. The carousel is then rotated to move the next sample collection cup into a position to receive a subsequent mixed soil sample.

All functions of the soil sampling apparatus may be controlled from a remote control panel, typically located adjacent the driver of the tow vehicle. A closed circuit television monitor located adjacent the remote control panel and connected to a camera disposed on the soil sampling apparatus is provided to allow the operator to visually monitor the operation of the soil sampler.

Figure 1:
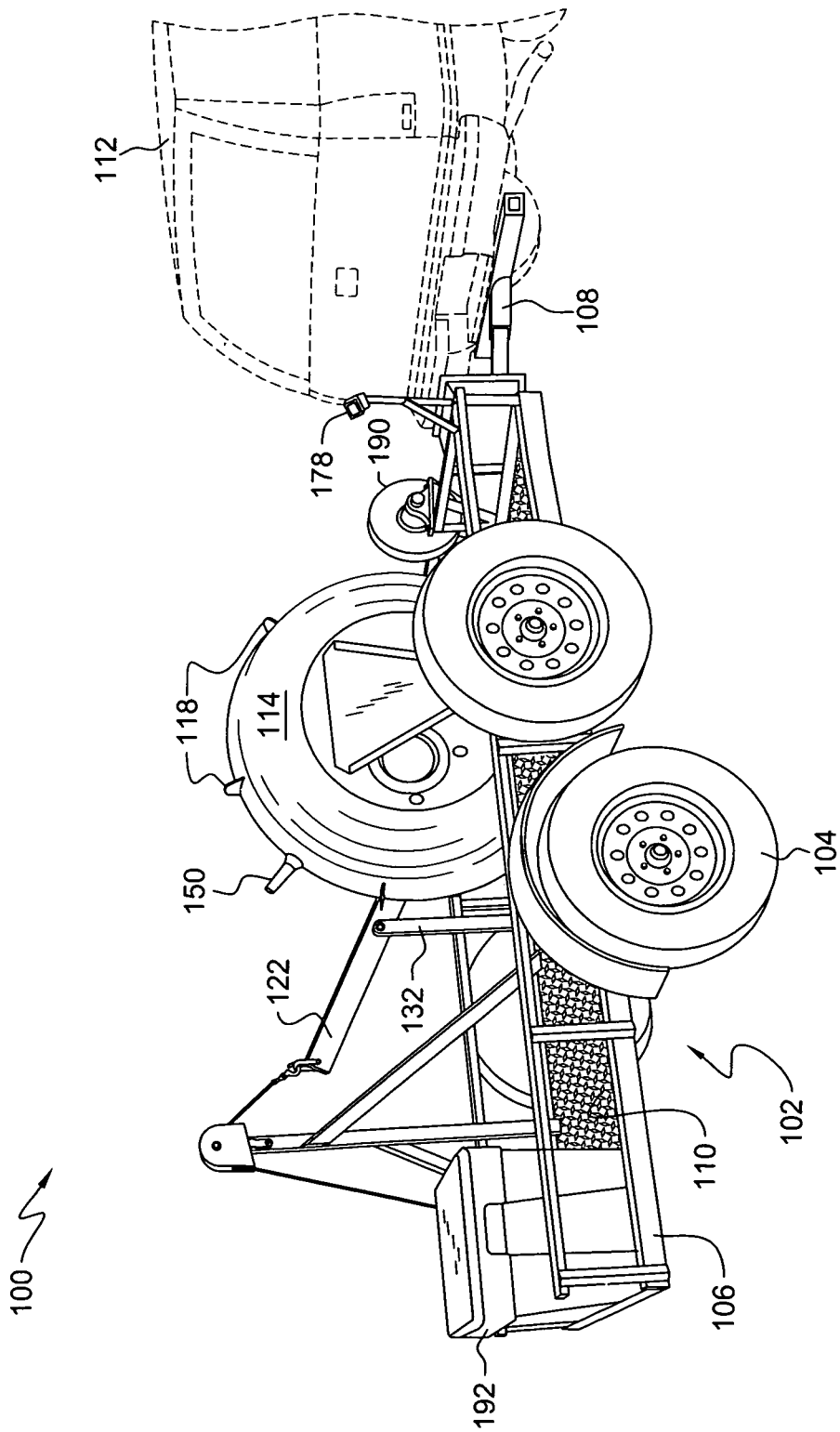
FIG. 1 is a right side elevational view of the soil sampling apparatus of the invention.
Figure 2:
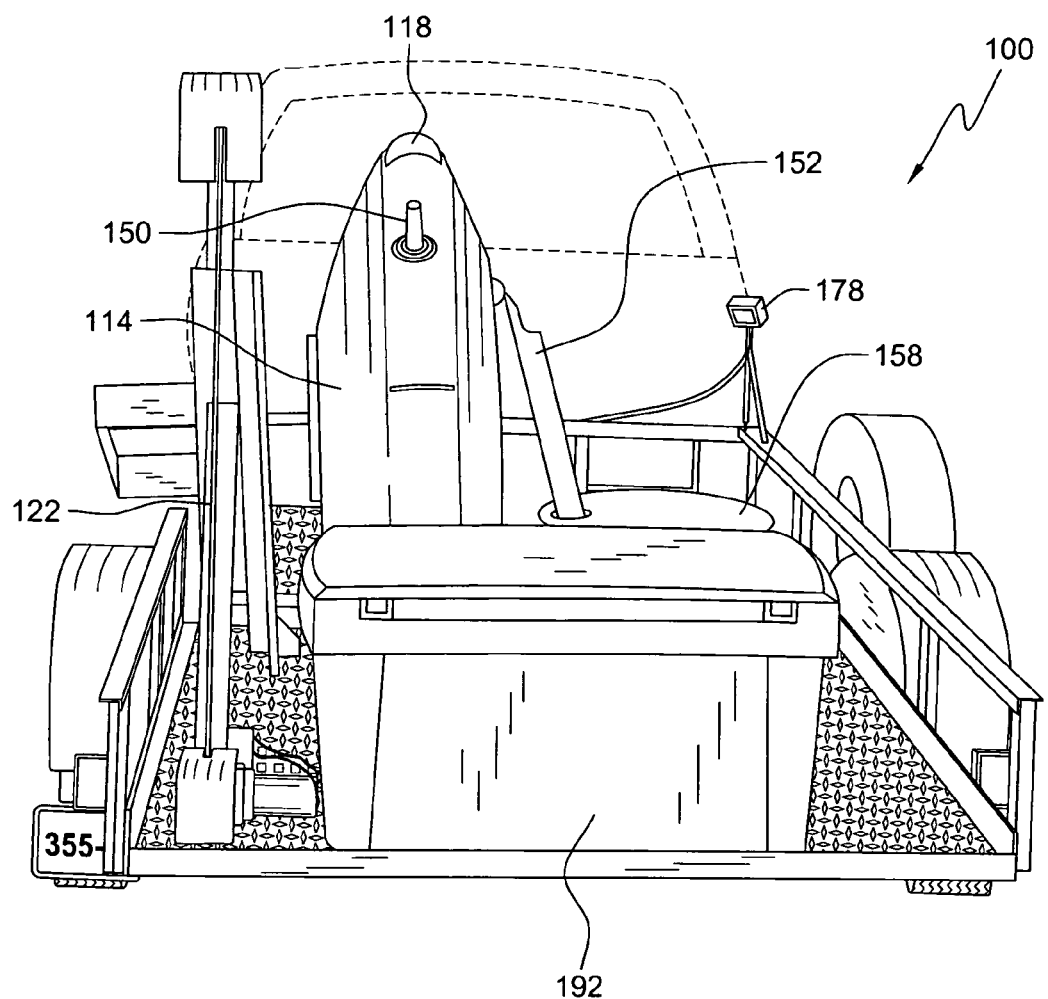
FIG. 2 is a rear elevational view of the soil sampling apparatus of FIG. 1.
Figure 3:
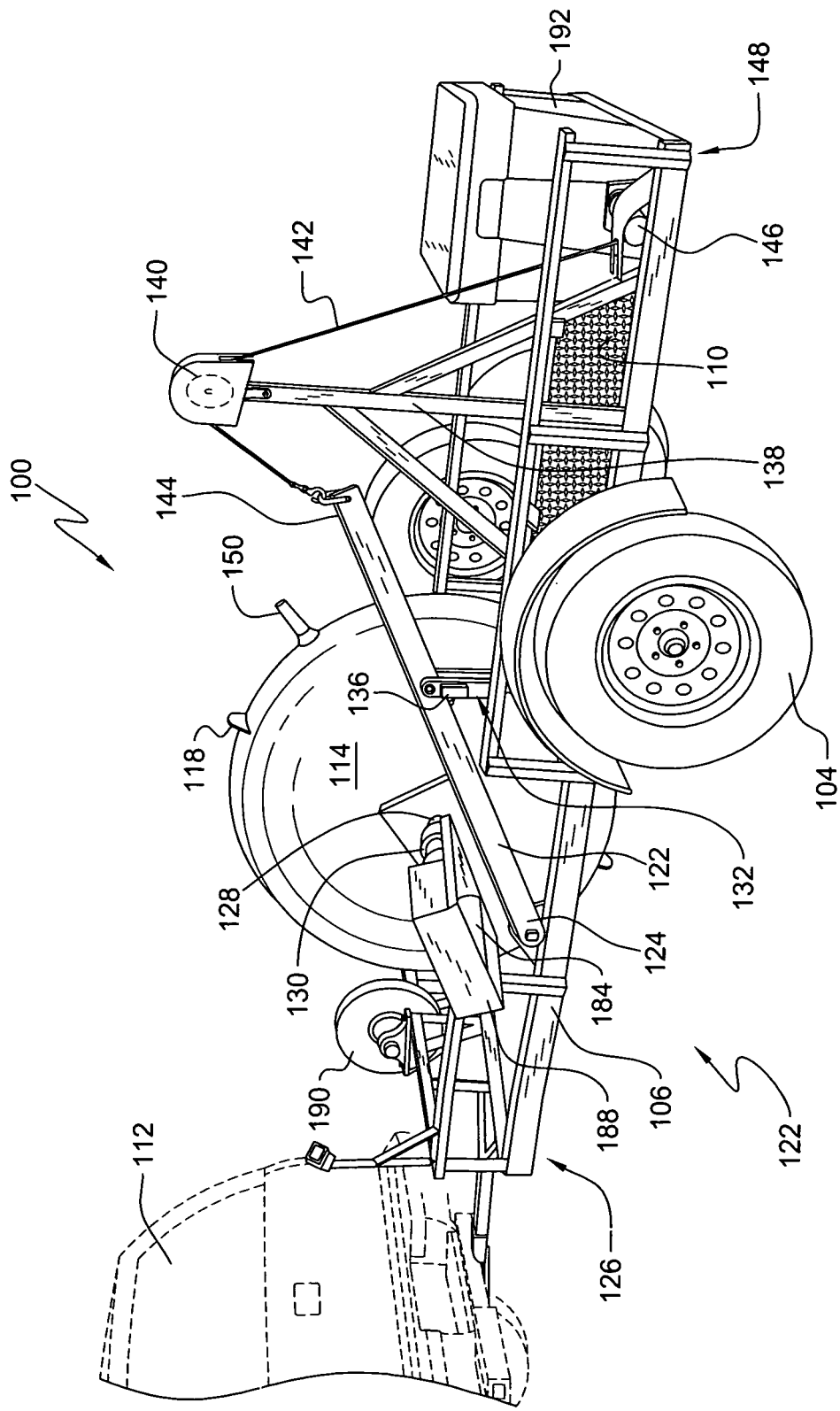
FIG. 3 is a left side elevational view of the soil sampling apparatus of FIG. 1.

Referring first to FIGS. 1, 2, and 3, there are shown right, rear, and left elevational schematic views, respectively, of an embodiment of the soil sampling apparatus in accordance with the invention, hereinafter the soil sampler, generally at reference number 100.

Soil sampler 100 is supported on a trailer 102 having a frame 106 having a tongue with a hitch 108 at a distal end thereof adapted for removable interconnection to a tow vehicle 112, a pair of wheels 104, and all other features (e.g., tail/brake lights, turn indicators, running lights, etc., none of which are shown) that allow trailer 102 to be legally moved on a road or highway. It will be recognized that soil sampler 100 may alternately be supported on a self propelled vehicle such as a truck, not shown.

It should be recognized that tow vehicle 112 forms no part of the present invention and is shown merely to illustrate soil sampler 100 in its intended operational environment. Tow vehicle 112 may be any vehicle adapted to traverse the land to be sampled and capable of pulling soil sampler 100. Typical tow vehicles 112 include tractors, all-wheel drive trucks, or other such vehicles. It will be further recognized that trailer 102 may be moved from one location to another by any vehicle capable of pulling a trailer, not necessarily a vehicle capable of pulling soil sampler 100 across ground to be sampled.

Trailer frame 106 is typically an elongated rectangular structure having a flat bed or floor 110 typically selectively formed from a combination steel plate or steel mesh. Steel mesh is used as a trailer floor in those areas where sampled dirt may spill and accumulate. A steel mesh floor in these areas of the trailer 102 bed 110 allows any spilled dirt, not shown, to fall through the floor 110.

A thin hollow drum 114 is aligned substantially parallel to a major axis of trailer frame 106. Drum 114 is rotatively affixed to a pivot arm 122 that has a proximal end 124 pivotally affixed to trailer frame 106 proximate a front left corner 126 thereof. In the embodiment chosen for purposes of disclosure, drum 114 has a closed left side to which an axle 128 is centrally affixed. A cross-section of hollow drum 114 is curvilinear. It will be recognized that other cross sectional shapes, for example, a V-shape may be substituted for the curvilinear cross sectional shape chosen for purposes of disclosure. Consequently, the invention is not considered limited to the curvilinear cross sectional shape chosen for purposes of disclosure. Rather, the invention is intended to include any suitable cross section shapes for hollow drum 114.

Axle 128 rotates in bearings 130 attached to pivot arm 122. Drum 114 is therefore, cantilevered from pivot arm 122. It will be recognized that in alternate embodiments alternate mounting arrangements may be substituted for the cantilevered arrangement chosen for purposes of disclosure. Consequently, the invention is not considered limited to the disclosed drum mounting arrangement. Rather, the invention is intended to include any suitable drum mounting arrangement.

Figure 4A:
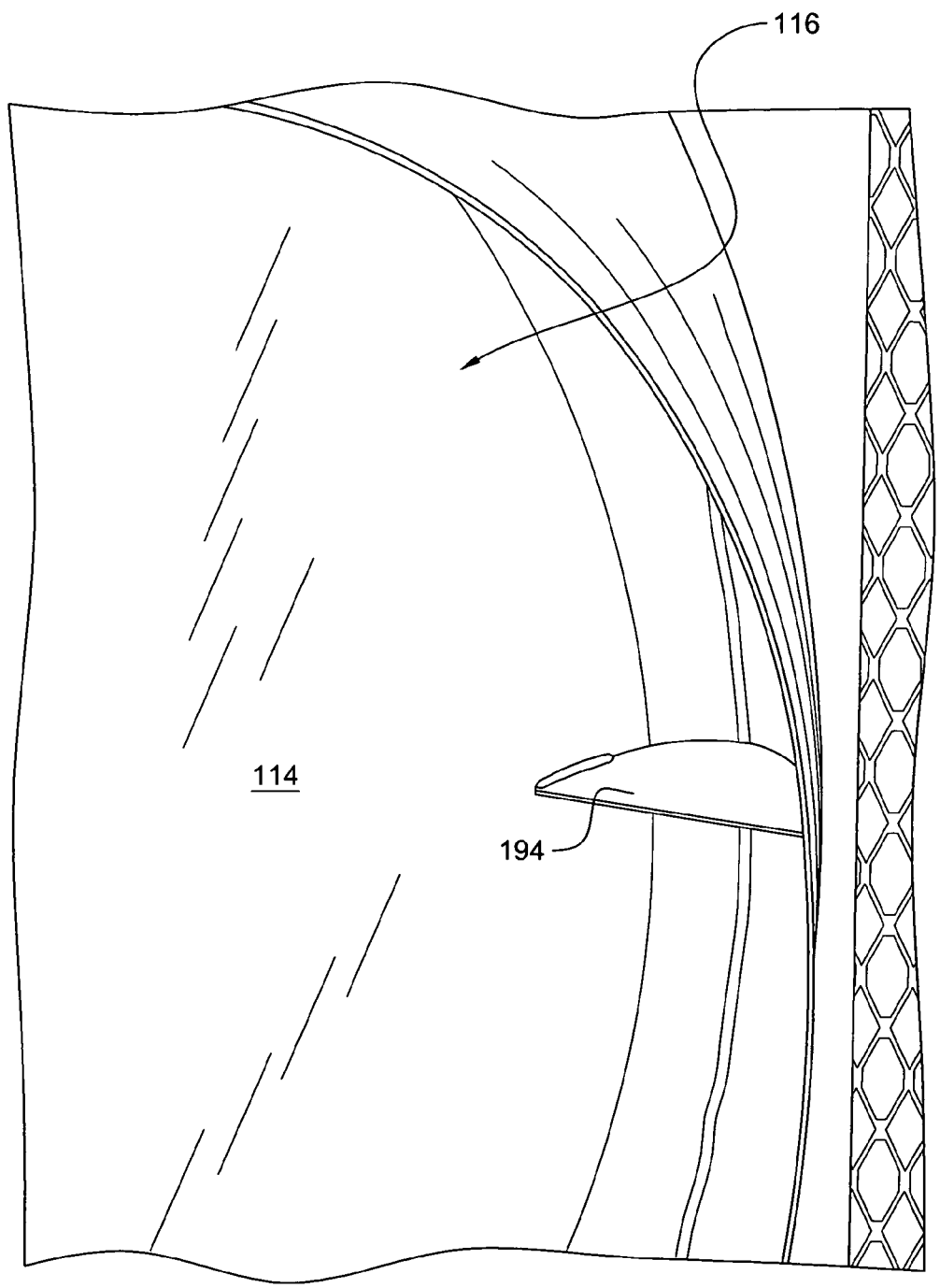
FIG. 4a is a detailed left elevational view of a portion of a soil collection and mixing drum forming part of the soil sampling apparatus of FIGS. 1, 2, and 3.

Referring now also to FIG. 4a, hollow drum 114 has a large opening 116 disposed in a right side thereof. A series of outwardly-pointing, ground-engaging drive protrusions of blades 118 are disposed externally around the central perimeter of hollow drum 114.

A stanchion 132 having a pair of spaced-apart vertical members, not specifically identified, allows pivot arm 122 to move vertically therebetween. Limit switch 136 disposed near an upper end of stanchion 132 is disposed to interact with pivot arm 122 to limit vertical movement of drum 114 between a lowered, operational position and a predetermined raised, stored position controlled by limit switch 136.

A pulley support frame 138 supports a pulley 140 proximate the top thereof. A cable 142 is attached to a distal end 144 of pivot arm 122 and is threaded over pulley 140 and, subsequently, to a winch 146 adapted to wind and unwind cable 142 thereto and therefrom. Winch 146 is typically attached to trailer frame 106 proximate a left rear corner 148 thereof and, typically is electrically powered.

A drum drive motor 184 disposed adjacent to and operatively connected to drum axle 128 is provided to rotated drum 114 when it is in a raised, non-sampling position. Drum drive motor 186 is disposed under a protective weather cover and safety shield 188.

An interchangeable, hollow, tapered probe 150 protrudes outwardly from the central perimeter of drum 114. Probe 150 is communicative with the interior of drum 114. As may best be seen in FIG. 4a, one or more mixing blades 136 are disposed on an inside perimeter of drum 114

Figure 4B:
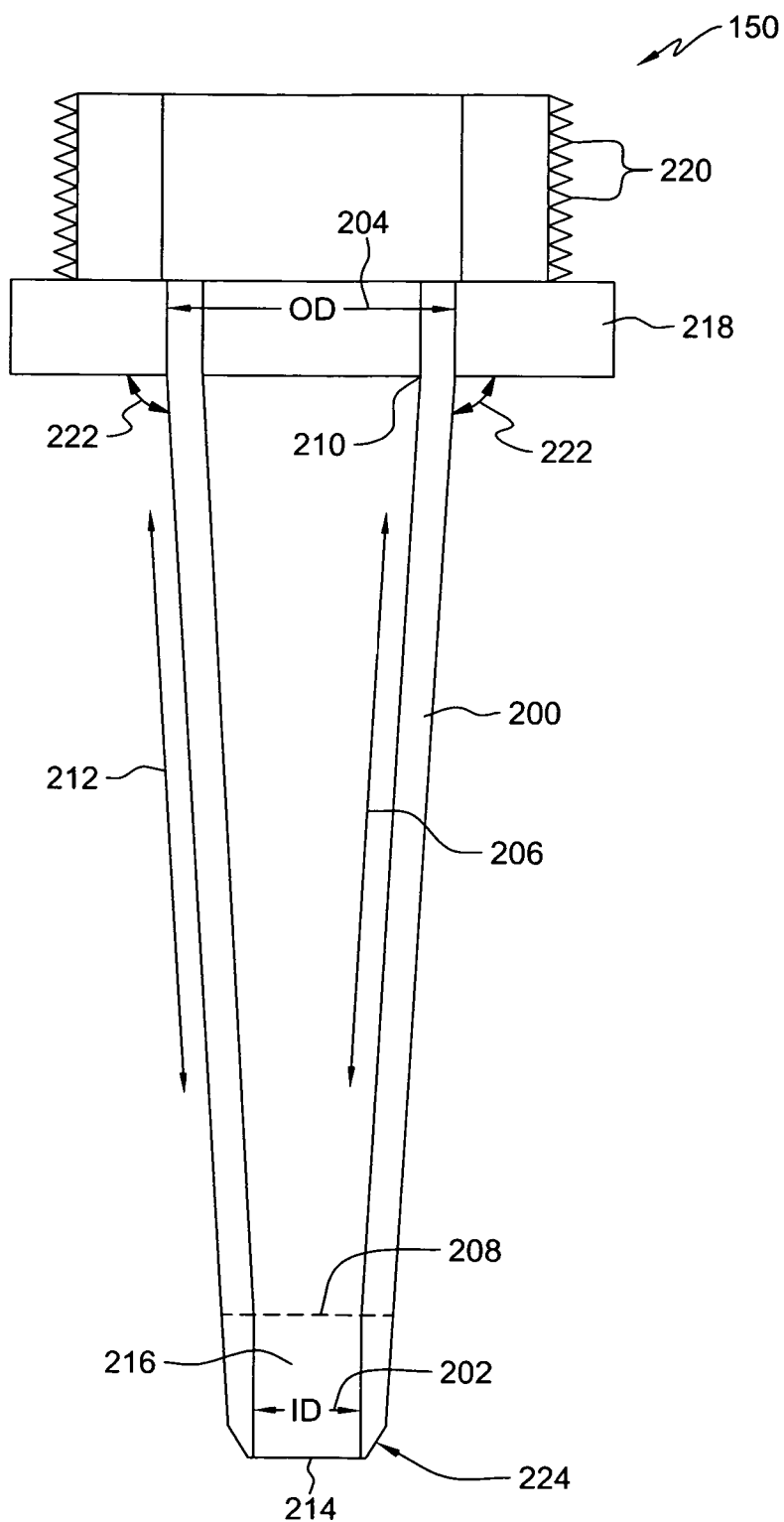
FIG. 4b is a detailed cross-sectional, elevational view of the soil probe of FIG. 2.

Referring now also to FIG. 4b, there is shown a detailed cross-sectional, elevational view of soil probe 150. Soil probe 150 is formed from a cylindrical pipe 200 having an inside diameter (ID) 202 and an outside diameter 204. An interior taper 206 is formed on a portion of an inner surface, not specifically identified, of cylindrical pipe 200 between a lower point 208 and an upper point 210. An external taper 212 is formed on an external surface, not specifically identified, of cylindrical pipe 200 between point 210 and tip 214. The interior region 216 between point 208 and tip 214 is cylindrical and represents the smallest interior diameter of soil probe 150.

A chamfer 224 may be formed adjacent tip 214 of soil probe 150 to facilitate penetration of soil probe 150 into the ground, not shown, being sampled.

The upper end of soil probe 150 is formed from a hex bushing 218 having exterior threads 220 adapted for removable connection with threads, not shown, forming a part of hollow drum 114.

An upper end of cylindrical pipe 200 is inserted into hex busing 218. A weld 222 forms a seal between hex bushing 218 and an outer surface, not specifically identified, of cylindrical pipe 200, thereby securing cylindrical pipe 200 to hex bushing 218.

Probe 150 is typically screwed or otherwise removably attached to drum 114 to allow ease of replacement. Probes 150 having different diameters and/or different lengths may be provided to meet any particular operating circumstance or environment. Different soil types may require different diameters for probe 150. Different sampling requirements may also determine the length of probe 150 required. Probe 150 may be replaced when wear due to usage or damage so requires.

As mentioned hereinabove, drum 114 is movable between a lowered, operative, ground-engaging position wherein the weight of drum 114 holds drum 114 against the ground, and a raised non-operative, stored position created when winch 146 winds cable 142 thereby raising distal end 144 of pivot arm 122. Pivot arm 122 functions as a class 2 lever, its load (i.e., drum 114) located between its fulcrum (i.e., rotatively affixed proximate end 124) and with the force applied thereto by winch 146 via cable 142 to distal end 144.

Figure 5:
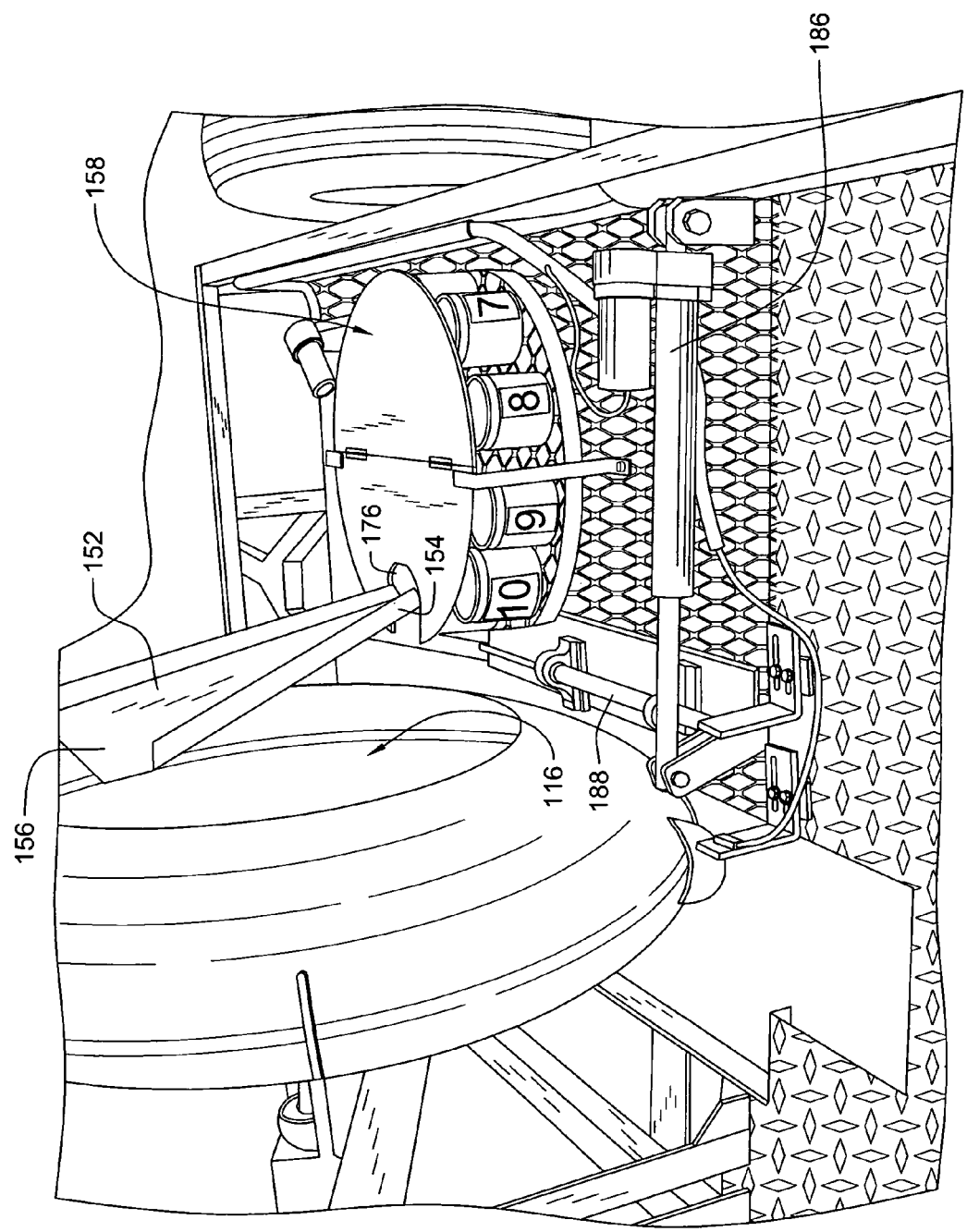
FIG. 5 is a detailed top rear perspective view of a portion of the soil sampler FIGS. 1, 2, and 3.
Figure 6:
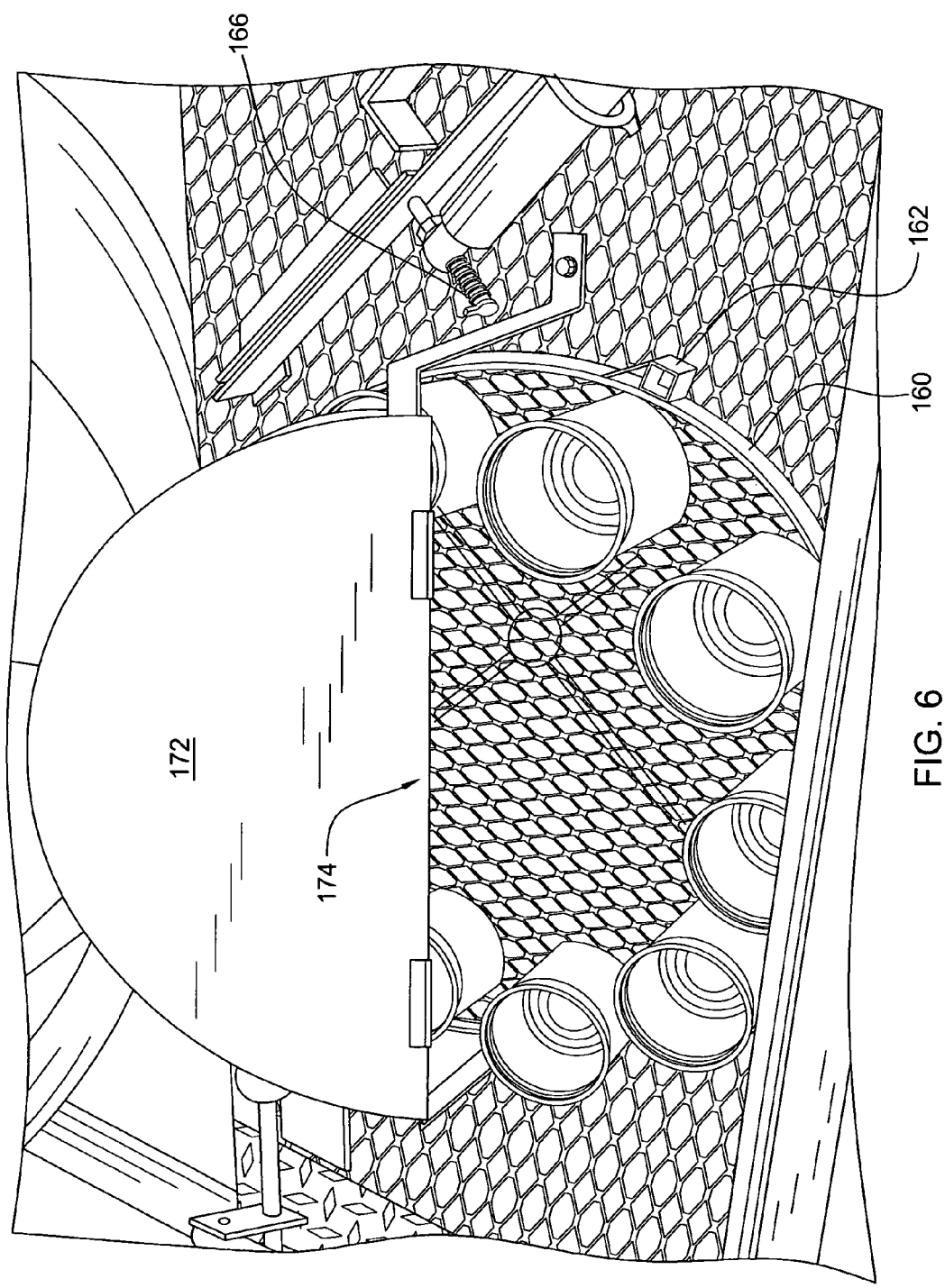
FIG. 6 is a top plan view of a portion of the soil sampler 100 of FIGS. 1, 2, and 3.

Referring now also to FIGS. 5 and 6, there are shown a detailed top rear perspective view and a top plan view, respectively of a portion of the soil sampler 100 of FIGS. 1, 2, and 3. A movable chute 152 having a major axis, not specifically identified, disposed substantially orthogonally to the major axis of trailer frame 106 is pivotally affixed to bed 110 of trailer 102 near a proximal end 154 of chute 152. A distal end 156 of chute 152 may selectively enter opening 116 of drum 114 such that sampled soil, not specifically identified, within drum 114 falls onto chute 152 as drum 114 rotates. Chute 152 is selectively moved into and withdrawn from an interior region of drum 114 by a chute actuator 186 and an intermediate mechanism 188 operatively attached to actuator 186 and chute 152.

A soil sample collection carousel 158 is provided adjacent proximal end 154 of chute 152. Carousel 158 has a circular platform 160 disposed horizontally and rotatively affixed to trailer bed 110. Detents 162 regularly spaced around the perimeter of circular horizontal platform 160 perform two functions. First, detents 162 interact with a pawl 164 to prevent reverse rotation of horizontal circular platform 160. Pawl 164 may best be seen in FIG. 7.

Figure 7:
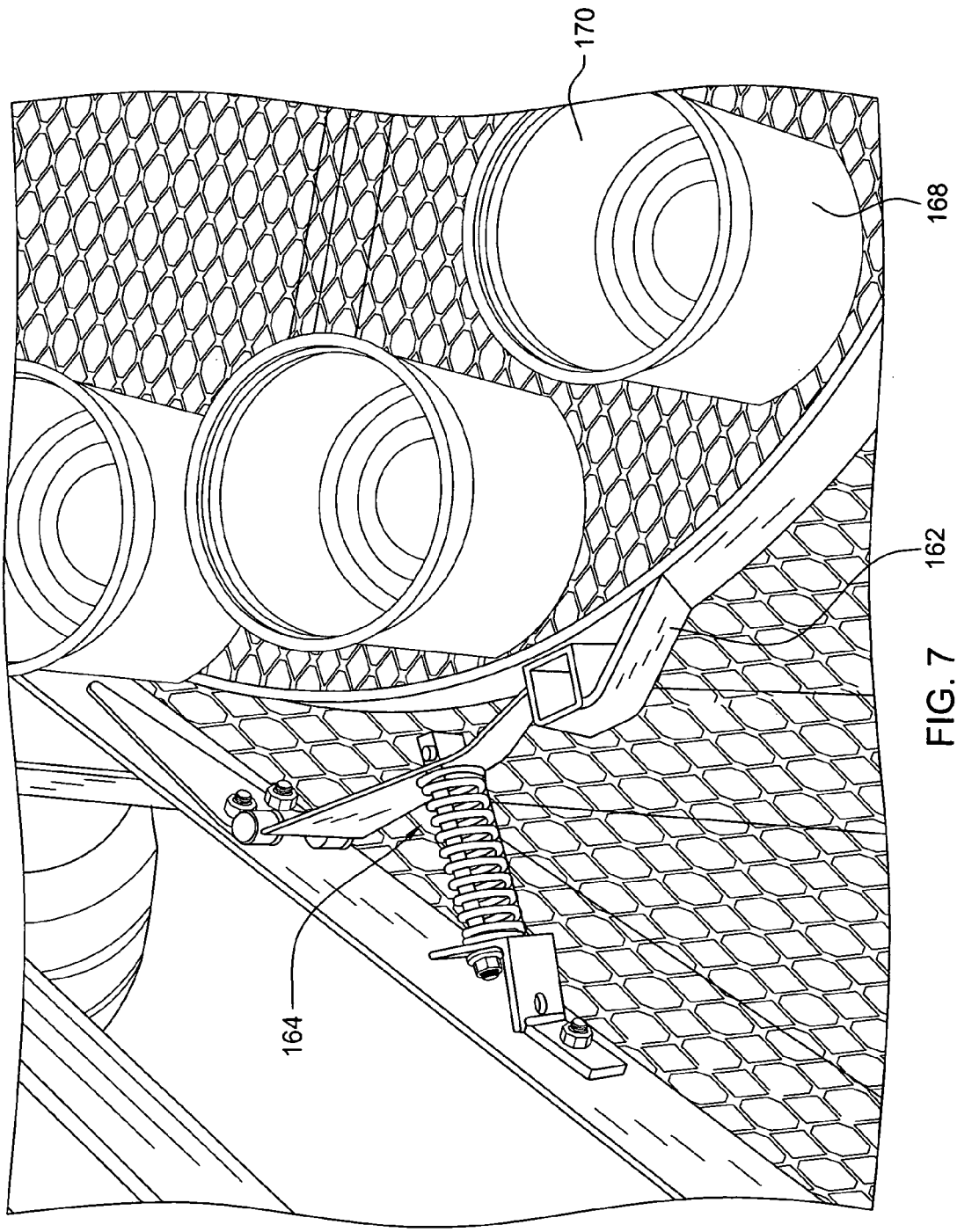
FIG. 7 is a detailed top perspective view of detent and pawl mechanism forming a portion of a sample collection carousel of FIGS. 6 and 7.

In addition, detents 162 provide a surface against which an electrically actuated platform advance pusher 166, best seen in FIG. 7, acts to advance horizontal circular platform 160 a predetermined number of degrees.

Mounted on an upper surface of circular horizontal platform 160 are a series of equidistantly spaced-apart sample cup holding receptacles 168. Sample cup holding receptacles 168 are typically open, hollow cylinders each having an inside diameter sized to receive a sample cup 170. Each sample cup holding receptacle 168 bears indicia on an outer surface thereof, typically a number to allow later identification of samples received therein. The spacing of sample cup receptacles and detents 168 is matched to successively position a sample cup 170 under proximal end 154 of chute 152 such that sampled soil from within drum 114 may be discharged thereinto.

In the embodiment chosen for purposes of disclosure, soil collection carousel 158 supports ten labeled sample cup holding receptacles 168. It will be recognized that other numbers of sample cup holding receptacles 168 could be used with suitable modifications to other system components. Consequently, the invention is not considered limited to the ten sample cup holding receptacles 168 chosen for purposes of disclosure. Rather the invention is intended to include fewer or additional sample cup holders.

It will further be recognized that sample collection systems other than circular platform 160 might be substituted therefor. The invention is intended to cover any such sample collection systems.

In still other embodiments, each sample could be packaged directly in a plastic bag, not shown, or other similar sample container and each bag identified with indicia provided by an ink jet printer or a similar mechanism.

Carousel 158 has a circular cover 172 that may be hinged along a midpoint 174 thereof. Circular cover 172 typically has an opening 176 therein to allow sampled soil discharged from drum 114 via chute 152 to pass through cover 176 into a sample cup 170 positioned on circular horizontal platform 160 positioned therebelow.

Figure 8:
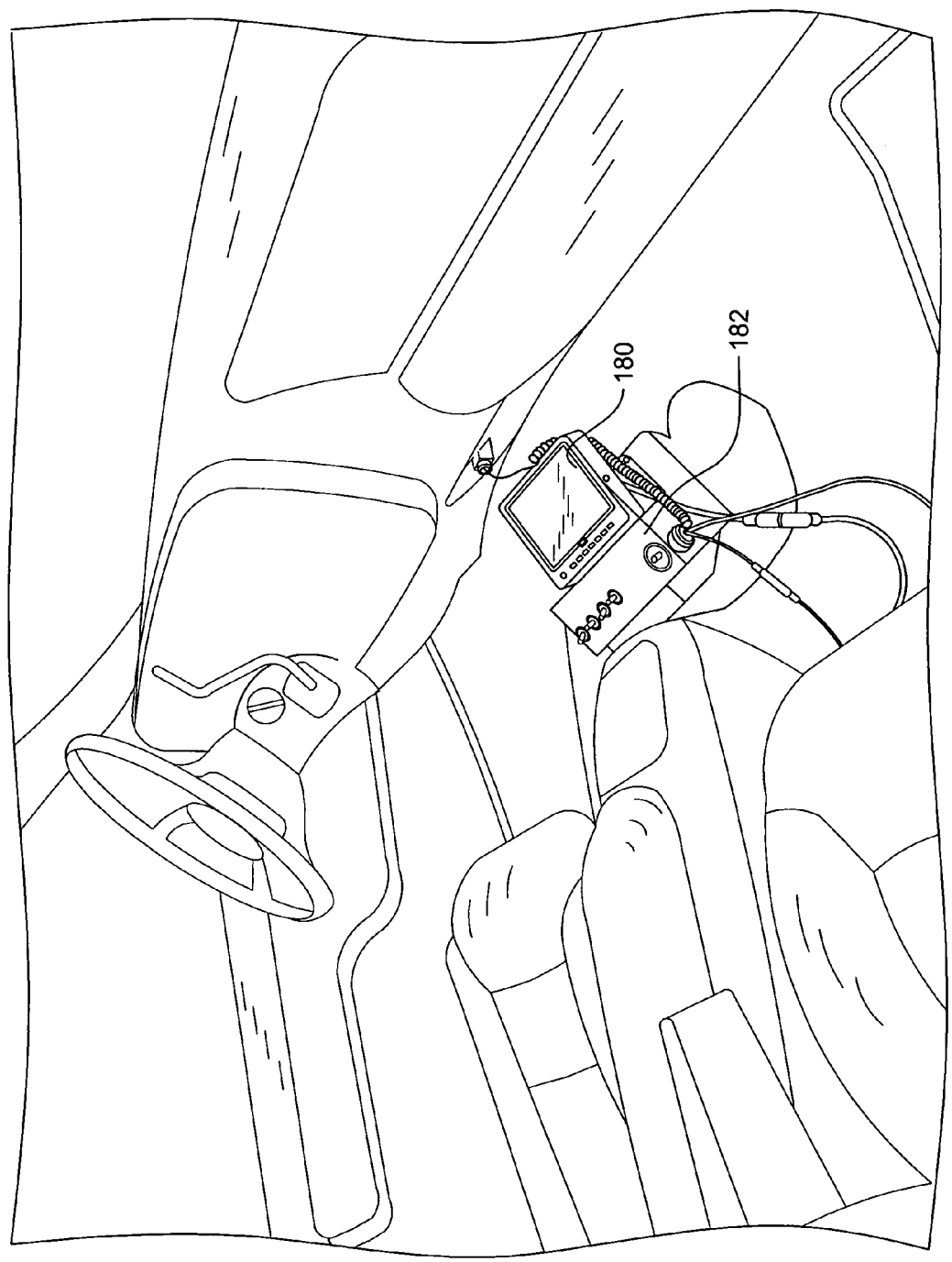
FIG. 8 is a side perspective view of a control panel and television monitor in accordance with the invention.

A television camera 178 is mounted near the front of trailer 102 and typically aimed to view the contents of hollow drum 114 while soil sampler 100 is in operation. A TV monitor 180 is typically disposed adjacent a driver, not shown, of tow vehicle 112 and also adjacent a control panel 182 that allows the driver of tow vehicle 112 to control the operation of the elements of soil sampler 100. Remote control 182 and television monitor 178 are best seen in FIG. 8.

A probe brush 190 is disposed forward of drum 114 and spaced such that a distal end of probe 150 brushes probe brush 190 whereby any soil clinging within probe 150 is released.

In alternate embodiments, two options may be added to the exterior of drum 114. First, a coulter blade, not shown, may be affixed to drum 114 to prepare soil ahead of probe 150 thereby allowing a soil core sample to be more readily removed.

In a second alternate embodiment, a row cleaner, not shown, such as a device placed forward of a planting drill may be used to remove or displace surface debris such as corn stalks that could interfere with the operation of soil sampler 100.

In operation, soil sampler 100 is driven to a field or other plot of land to be sampled, neither shown, by tow vehicle 112. When in position to begin sampling, winch 146 is actuated from control panel 182. Operating winch 146 allows pivot arm 122 carrying hollow drum 114 to be lowered to a ground-engaging, operational position. Tow vehicle 112 is moved forward and hollow drum 114 revolves as ground-engaging protrusions 118 cause hollow drum 114 to revolve as tow vehicle 112 moves forward.

As drum 114 revolves, hollow tapered probe 150 pierces the ground and removes a soil sample thereof. Further rotation of hollow drum 114 brings it to an orientation where gravity causes the earth sample within hollow tapered probe 150 to fall into an interior region of hollow drum 114. The process continues until a desired region of the field being sampled has been traversed.

As hollow drum rotates, mixing blade 120 functions to help blend the accumulating soil sample within hollow drum 114.

When a desired region of the field being sampled has been traversed, hollow drum 114 is raised by again actuating winch 146. When hollow drum 114 has been raised, drum rotation motor 184 is started from remote control panel 182 and hollow drum 114 is rotated for a time sufficient to ensure that the soil samples within hollow drum 114 are thoroughly blended. Chute 152 is then actuated from remote control panel 186 and is moved into the interior of hollow drum 114 so as to receive the blended soil sample at its distal end 156.

As hollow drum 114 is rotated, soil carried to the zenith falls onto chute 152 and slide down chute 152 to proximal end 154 thereof positioned adjacent cover opening 176 and the sampled soil sliding down chute 152 is discharged into a sample cup 170 positioned directly therebelow.

When the entire soil sample is discharged into a sample cup 170, chute 152 is withdrawn from within hollow drum 114.

Platform advance pusher 166 is actuated from remote control panel 182 and circular platform 160 is rotated to the next detent position.

When all sample cups have been filled by successive sampling runs, the sample cups 170 are emptied into individual labeled bags, not shown, and the bags are stored for transport to a soil analysis facility. Sample cups 170 may be discarded or may be cleaned and replaced in sample cup holding receptacles as desired.

An optional storage container 192 may be disposed on trailer 102.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A soil sampling system for collecting and retaining multiple soil samples, comprising:
   a) a mobile platform for traversing a region from which soil samples are to be periodically extracted;
   b) a hollow, cylindrical drum supported upon and rotatively connected to said mobile platform, said drum having a central perimeter bearing a removable, outwardly projecting soil probe thereupon, said probe being communicative with an interior region of said hollow, cylindrical drum, said cylindrical drum having at least one mixing blade disposed on an interior perimeter thereof, and an opening in a vertical side thereof to allow selective entrance of a distal end of a soil collection chute into an interior region of said cylindrical drum;
   c) means for automatically removing a collected, blended soil sample from an interior region of said hollow, cylindrical drum supported upon said mobile platform and disposed adjacent a side of said hollow, cylindrical drum;
   d) means for receiving and individually retaining a plurality of said collected, blended soil samples disposed adjacent said means for automatically removing a collected soil sample.

2. The soil sampling system for collecting and retaining multiple soil samples as recited in claim 1, wherein said means for automatically removing a collected soil sample from an interior region of said hollow, cylindrical drum comprises a chute pivotably affixed to said mobile platform and movable between an operative position wherein a distal end of said chute is disposed within said interior portion of said hollow, cylindrical drum in a sample gathering orientation and a non-sample gathering orientation external to said interior region of said hollow, cylindrical drum.

3. The soil sampling system for collecting and retaining multiple soil samples as recited in claim 1, wherein said means for receiving and individually retaining a plurality of said collected, blended soil samples disposed adjacent said means for automatically removing a collected soil sample comprises a carousel comprising a circular, horizontal platform rotatively connected to a bed of said mobile platform and having a plurality of sample collection cups disposed on an upper surface thereof.

4. The soil sampling system for collecting and retaining multiple soil samples as recited in claim 3, further comprising a plurality of sample cup receptacles disposed intermediate said upper surface of said horizontal platform, each of said sample cup receptacles being affixed thereto and adapted to receive and removably support one of said plurality of sample collection cups therein.

5. The soil sampling system for collecting and retaining multiple soil samples as recited in claim 1, wherein said hollow drum is selectively movable between a lowered, ground-engaging position and a raised position.

6. The soil sampling system for collecting and retaining multiple soil samples as recited in claim 5, wherein said hollow drum is affixed to a pivot arm, a proximal end of said pivot arm being hingedly affixed to a bed of said mobile platform, and a distal end of said pivot arm being operationally connected to a winch, said hollow drum being rotatively affixed to said pivot arm intermediate said distal and said proximal ends thereof.

7. The soil sampling system for collecting and retaining multiple soil samples as recited in claim 6 wherein said operational connection between said distal end of said pivot arm and said winch comprises:
   i) a pulley support frame attached to at least one of members selected from the group consisting of: a frame of said mobile platform and a bed of said mobile platform and extending upwardly therefrom;
   ii) a pulley affixed to an upper portion of said pulley support frame; and
   iii) a cable extending from said distal end of said pivot arm to said winch, said cable passing over an outer surface of said pulley.

8. The soil sampling system for collecting and retaining multiple soil samples as recited in claim 5, wherein said hollow drum further comprises a drum drive motor operatively connected thereto and disposed to selectively rotate said hollow drum when said hollow drum is in said raised position.

9. The soil sampling system for collecting and retaining multiple soil samples as recited in claim 5, further comprising a probe brush disposed adjacent said hollow cylindrical drum and contacting a distal end of said removable, outwardly projecting soil probe when said hollow, cylindrical drum is in said raised position and said removable, outwardly projecting soil probe is rotated past said probe brush.

10. The soil sampling system for collecting and retaining multiple soil samples as recited in claim 1, wherein said outwardly projecting soil probe comprises a tapered soil probe.

11. The soil sampling system for collecting and retaining multiple soil samples as recited in claim 10, wherein said tapered, outwardly projecting soil probe comprises a double tapered soil probe.

12. The soil sampling system for collecting and retaining multiple soil samples as recited in claim 1, further comprising:
   e) a remote control assembly operatively connected to at least one selected from the group comprising: said means for automatically removing a collected sample and said means for receiving and individually retaining a plurality of said collected, blended soil samples.

13. The soil sampling system for collecting and retaining multiple soil samples as recited in claim 12, wherein said remote control assembly further comprises an electrical cable operatively connected between said remote control assembly and said at least one selected from the group comprising: said means for automatically removing a collected sample and said means for receiving and individually retaining a plurality of said collected, blended soil samples.

14. The soil sampling system for collecting and retaining multiple soil samples as recited in claim 12, further comprising:
- f) a television camera disposed on said mobile platform selectively aimed at at least one selected from the group comprising: said hollow, cylindrical drum, said means for automatically removing a collected sample and said means for receiving and individually retaining a plurality of said collected, blended soil samples; and
- g) a television monitor operatively connected to said television camera.

15. The soil sampling system for collecting and retaining multiple soil samples as recited in claim 14, wherein said television monitor is disposed proximate said remote control assembly.

* * * * *